(12) United States Patent
Kumta et al.

(10) Patent No.: US 10,881,332 B2
(45) Date of Patent: *Jan. 5, 2021

(54) DEGRADABLE CARBON NANOTUBE-CONTAINING BIOSENSORS AND METHODS FOR TARGET CLINICAL MARKER DETECTION

(71) Applicant: UNIVERSITY OF PITTSBURGH—OF THE COMMONWEALTH SYSTEM OF HIGHER EDUCATION, Pittsburgh, PA (US)

(72) Inventors: Prashant Nagesh Kumta, Pittsburgh, PA (US); Madhumati Ramanathan, Pittsburgh, PA (US); Mitali Shirish Patil, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/679,441

(22) Filed: Aug. 17, 2017

(65) Prior Publication Data

US 2017/0343543 A1 Nov. 30, 2017

Related U.S. Application Data

(62) Division of application No. 14/197,722, filed on Mar. 5, 2014, now Pat. No. 9,753,030.

(Continued)

(51) Int. Cl.
*A61B 5/145* (2006.01)
*A61B 5/053* (2006.01)
(Continued)

(52) U.S. Cl.
CPC .......... *A61B 5/14503* (2013.01); *A61B 5/053* (2013.01); *A61B 5/14546* (2013.01);
(Continued)

(58) Field of Classification Search
None
See application file for complete search history.

(56) References Cited

U.S. PATENT DOCUMENTS

| 2003/0148272 A1* | 8/2003 | Rosenquist | G01N 33/53 435/6.13 |
| 2003/0204062 A1* | 10/2003 | Ohashi | C07K 16/40 530/388.26 |

(Continued)

OTHER PUBLICATIONS

Quinn et al. Electrodeposition of Noble Metal Nanoparticles on Carbon Nanotubes, Apr. 2005, JACS, vol. 127, pp. 6146-6147.

*Primary Examiner* — Melanie Brown
(74) *Attorney, Agent, or Firm* — Eckert Seamans Cherin & Mellott; Carol A. Marmo

(57) ABSTRACT

The invention relates to carbon nanotube-containing composites as biosensors to detect the presence of target clinical markers, methods of their preparation and uses in the medical field. The invention is particularly suitable for the detection in patient biological specimens of bone markers and tissue markers. The biosensors of the invention include carbon nanotubes deposited on a substrate, gold nanoparticles deposited on the carbon nanotubes and, binder material and biomolecule deposited on the gold-coated carbon nanotubes. The biomolecule is selected to interact with the target clinical markers. The biosensor can be used as an in-situ or an ex-situ device to detect and measure the presence of the target clinical markers.

9 Claims, 2 Drawing Sheets

Related U.S. Application Data

(60) Provisional application No. 61/773,350, filed on Mar. 6, 2013.

(51) Int. Cl.
*C12Q 1/42* (2006.01)
*A61B 5/1473* (2006.01)
*A61B 5/00* (2006.01)
*B82Y 15/00* (2011.01)

(52) U.S. Cl.
CPC ........ *A61B 5/14735* (2013.01); *A61B 5/4504* (2013.01); *C12Q 1/42* (2013.01); *A61B 2562/0285* (2013.01); *A61B 2562/0295* (2013.01); *A61B 2562/12* (2013.01); *B82Y 15/00* (2013.01); *Y10S 977/748* (2013.01); *Y10S 977/92* (2013.01)

(56) References Cited

U.S. PATENT DOCUMENTS

| | | |
|---|---|---|
| 2004/0167014 A1 | 8/2004 | Yan et al. |
| 2005/0274612 A1 | 12/2005 | Segawa et al. |
| 2007/0258880 A1 | 11/2007 | Murakoshi |
| 2009/0084678 A1 | 4/2009 | Joshi et al. |
| 2010/0009432 A1 | 1/2010 | Lee et al. |
| 2010/0023132 A1 | 1/2010 | Imran |
| 2012/0135540 A1 | 5/2012 | Bruno |
| 2013/0261735 A1 | 10/2013 | Pacetti et al. |
| 2014/0147444 A1 | 5/2014 | Deshpande et al. |
| 2014/0206958 A1 | 7/2014 | Laramy et al. |
| 2014/0357964 A1 | 12/2014 | Wisniewski et al. |
| 2015/0335741 A1 | 11/2015 | Smeltzer et al. |

\* cited by examiner

DEGRADABLE CARBON NANOTUBE-CONTAINING BIOSENSORS AND METHODS FOR TARGET CLINICAL MARKER DETECTION

CROSS REFERENCE TO RELATED APPLICATIONS

This application is a divisional of, and claims the benefit of priority to U.S. patent application Ser. No. 14/197,722, filed Mar. 5, 2014, entitled "DEGRADABLE CARBON NANOTUBE-CONTAINING BIOSENSORS AND METHODS FOR TARGET CLINICAL MARKER DETECTION" and under 35 U.S.C. § 119(e) to U.S. Provisional Patent Application Ser. No. 61/773,350, filed Mar. 6, 2013, entitled "Degradable Osteosensor (DOS): Novel Degradable CNT Based Impedimetric Biosensors for Bone Marker Detection", the contents of which are herein incorporated by reference.

GOVERNMENT SUPPORT

The invention was made with government support under grant #0812348 awarded by the National Science Foundation. The government has certain rights in the invention.

FIELD OF THE INVENTION

The invention relates to carbon nanotube-containing composites as biosensors to detect the presence of tissue clinical markers, methods of their preparation and uses in the medical field. The invention is particularly suitable for the detection in patient biological specimens of tissue clinical markers generated as a result of tissue resorption in the body of the patient.

BACKGROUND OF THE INVENTION

Millions of individuals suffer from various forms of musculoskeletal disorders, such as bone carcinoma and osteoporosis. When these disorders are not treated properly, they can lead to further complications, some of which may be fatal. The yearly costs arising from musculoskeletal disorders and osteoporosis-related fractures in the United States has been estimated as billions of dollars and these costs are projected to increase. Thus, there is a desire and a need to detect and monitor any changes in bone metabolism to effectively treat bone diseases during the early stages of their development. Bone turnover marker levels reflect such changes in bone metabolism, including instances in which old bone is being replaced with new bone during abnormal bone metabolism. The bone turnover markers are classified as those pertaining to bone formation, which reflects osteoblastic activity; or those contributing to bone resorption, which reflect osteoclastic activity. These markers can serve as a tool to monitor the progression of disease, thus allowing for early treatment to be administered for effective prognosis.

In addition to bone markers, there is a desire in the art to detect and monitor other clinical markers. As an example, tissue clinical markers would serve as a tool to detect and monitor the changes in various organs, such as but not limited to, the heart.

Various conventional analytical techniques are known in the art to detect clinical markers, including ELISA and radioimmunoassay. Although highly sensitive, these techniques suffer from disadvantages of being time consuming, expensive, bulky and requiring skilled personal for operation. The associated disadvantages limit the use of these techniques in hospitals and clinics. Other techniques have been developed to overcome these disadvantages. For example, biosensors have been developed which exhibit quick response times, are less expensive, small, portable, and easy to use, thereby making them amenable to point-of-care testing. There are known in the art fluorescence-based sensing devices and impedence-based sensing devices. In particular, impedance-based devices are extremely sensitive to interfacial binding events occurring at the probe surface.

Among the various materials used in the development of biosensors, carbon nanotubes (CNTs) are suitable materials due to their exceptional mechanical, electrical and surface properties. Further, the approach for CNT growth allows for conditions to be modified to achieve specific properties to fit the needs for sensor integration.

There is a need in the art to develop CNT-based biosensors for the detection of clinical markers, such as bone markers and tissue markers. Further, it is desired to develop biosensors that may be employed ex-situ and in-situ. Furthermore, for in-situ biosensors, it is desired to develop a biosensor that is degradable over a reasonable period of time.

SUMMARY OF THE INVENTION

In one aspect, the invention provides a degradable biosensor composite to detect a clinical marker in a body of a patient. The biosensor includes a substrate having a surface, a plurality of carbon nanotubes having a surface and deposited on the surface of the substrate, a plurality of gold nanoparticles electrodeposited on the surface of the plurality of carbon nanotubes to form gold-coated nanotubes, a binding material adsorbed on the plurality of gold nanoparticles which is selected to bind biotinylated biomolecule, and the biotinylated biomolecule deposited on the gold-coated nanotubes which is selected to interact with the target clinical marker.

The target clinical marker can be selected from bone marker and tissue marker. Further, the target clinical marker can be selected from c-terminal telopeptide, n-terminal telopeptide, alkaline phosphatase, Troponin I and myoglobin.

The biotinylated biomolecule can be selected from biotinylated antibody and aptamer. In certain embodiments, the biotinylated biomolecule can be selected from aptamer specifically for c-terminal telopeptide, n-terminal telopeptide, alkaline phosphatase, Troponin I and myoglobin. In certain other embodiments, the biotinylated biomolecule can be selected from c-terminal telopeptide antibody, n-terminal telopeptide antibody, alkaline phosphatase antibody, Troponin I antibody and myoglobin antibody.

The biosensor can be deposited or embedded on a surface of a degradable implant device. The implant device can be a degradable scaffold. The degradable scaffold can be composed of a magnesium alloy.

The substrate of the biosensor can be the surface of a degradable implant device. The implant device can be a degradable scaffold. The degradable scaffold can be composed of a magnesium alloy.

The binding material can be selected from the group consisting of avidin, neutravidin and mixtures thereof.

In certain embodiments, the substrate can be selected from the group consisting of silicon and silicon-containing materials.

In certain embodiments, the target clinical marker is effective to detect bone resorption in the body of the patient.

In another aspect, the invention provides a method of preparing a degradable biosensor composite to detect a target clinical marker in a body of a patient. The method includes providing a substrate having a surface, depositing a plurality of carbon nanotubes having a surface on the surface of the substrate, electrodepositing a plurality of gold nanoparticles on the surface of the plurality of carbon nanotubes to form gold-coated nanotubes, adsorbing a binding material on the surface of the gold nanoparticles which is selected to bind biotinylated antibody or aptamer, selecting the biotinylated antibody or the aptamer to interact with the target clinical marker, and depositing the biotinylated antibody or the aptamer on the gold-coated nanotubes.

The carbon nanotubes can be deposited using chemical vapor deposition.

In yet another aspect, the invention provides a method for detecting a target clinical marker in a body of a patient. The method includes forming a biosensor composite as described above, contacting at least a portion of patient biological fluid with the biosensor composite, and employing a mechanism to identify the presence or absence of the target clinical marker.

In certain embodiments, the biosensor composite can be employed in-situ. In these embodiments, the method includes implanting the biosensor composite in the body of the patient, contacting the biosensor composite with patient biological fluid within the body of the patient, implanting a transmitting device in the body of the patient that is effective to generate impedimetric signals corresponding to the target clinical marker detected on the biosensor composite, providing a measuring device ex-situ to receive the impedimetric signals generated by the transmitting device and to convert the signals to determine the presence or absence of the target clinical marker, and providing a display device to identify the presence or absence of the target clinical marker.

In certain other embodiments, the biosensor composite can be employed ex-situ. In these embodiments, the method includes providing the biosensor composite in the form of a handheld device, removing the patient's biological fluid as a sample from the body, contacting at least a portion of the biological fluid sample with the handheld device, observing a visual change to the handheld device, and correlating the visual change with a chart or key to determine the presence or absence of the target clinical marker in the biological sample. The handheld device can be a test strip. The visual change can be a color change. Correlating the visual change can include comparing and matching the color change to the chart or the key which has various colors displayed thereon to identify various levels of the target clinical marker.

The mechanism of the method can be further employed to determine a concentration or range of concentration of the target clinical marker.

BRIEF DESCRIPTION OF THE DRAWINGS

A further understanding of the invention can be gained from the following description of the preferred embodiments when read in conjunction with the accompanying drawings in which.

DETAILED DESCRIPTION OF THE PREFERRED EMBODIMENTS

Figures 1A, 1B:
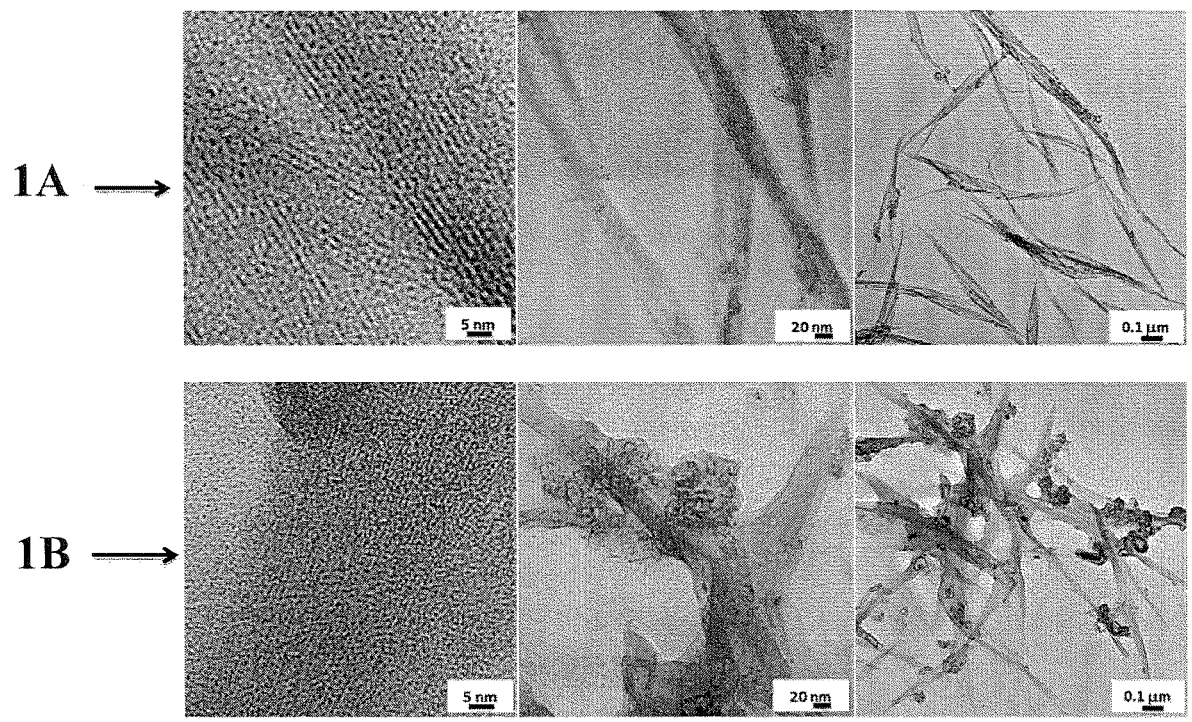
FIGS. 1A and 1B show TEM images of carboxylated CNTs without enzyme treatment and with enzyme treatment, respectively, in accordance with certain embodiments of the invention.

This invention relates to novel, degradable carbon nanotube-containing composites as impedimetric biosensors for clinical marker detection, methods for preparation and uses therefor. The clinical marker typically includes a target or pre-determined or pre-selected clinical marker of interest for detection. The target clinical marker can include bone marker and tissue marker. There are known various biomolecules that may be generated in a human body as a result of bone resorption or tissue resorption. Bone markers can include, but are not limited to, c-terminal telopeptide, n-terminal telopeptide and alkaline phosphatase. Tissue markers can include, but are not limited to, Troponin I and myoglobin. These examples of clinical markers are related to the heart, however, it is contemplated that the invention encompasses clinical markers relating to other tissues and organs with the human body. As a result of detecting the presence of target clinical markers, the biosensors of the invention are useful to determine bone and tissue resorption in a patient body. In particular, biosensors of the invention are useful to determine bone and tissue resorption resulting from implant devices in a patient body. There are various implant devices known in the art which include, but are not limited to, bone and tissue scaffolds.

The biosensors of the invention include a plurality of carbon nanotubes, e.g., a carbon nanotube array, having gold (Au) nanoparticles deposited thereon. The carbon nanotubes are produced, e.g., grown, in accordance with conventional methods and apparatus that are known in the art. For example, carbon nanotubes may be produced using various chemical vapor deposition (CVD) processes. In alternative embodiments, other vapor deposition techniques, such as pulsed laser deposition (PLD), radio frequency (RF) and direct current (DC) multi-target sputtering, liquid phase epitaxy, plasma enhanced CVD, and molecular beam epitaxy can be used. The deposition time can vary. The carbon nanotubes can be single-walled or multi-walled or combinations thereof. In general, carbon nanotubes are deposited or grown on a surface of a substrate. The carbon nanotubes can be vertically aligned on the substrate, e.g., perpendicular to the surface (planar surface) of the substrate. Various materials may be employed as the substrate. The substrate can include a current collector material. Non-limiting examples of suitable substrates include silicon (Si) or Si-containing material.

The Au nanoparticles are electrodeposited on the surface of the carbon nanotubes using conventional electro-deposition equipment and processes. The carbon nanotubes, e.g., array, having Au nanoparticles deposited thereon are functionalized such that a biomolecule, e.g., antibody or aptamer, attaches thereto. There are various conventional mechanisms for functionalizing the Au nanoparticles. In accordance with certain embodiments of the invention, the Au nanoparticles are functionalized by adsorbing a binding material thereon. The binding material is selected based on its capability to bind particular biomolecule, e.g., antibody or aptamer. Non-limiting examples of suitable binder materials include avidin and neutravidin. In certain embodiments, avidin is preferred. Further, the antibody or aptamer for binding to the avidin is selected based on its capability to interact with a target clinical marker. Non-limiting examples of suitable antibody or aptamer include biotinylated antibody or aptamer selected specifically for c-terminal telopeptide, n-terminal telopeptide, alkaline phosphatase, Troponin I and myoglobin. In certain other embodiments, the biotinylated biomolecule can be selected from c-terminal telopeptide antibody, n-terminal telopeptide antibody, alkaline phosphatase antibody, Troponin I antibody and myoglobin antibody. In certain embodiments, the biotinylated antibody is selected from the biotinylated biomolecule can be selected from aptamer specifically for c-terminal telopeptide, n-terminal telopeptide, alkaline phosphatase, Troponin I and myoglobin. In certain other embodiments, the biotinylated biomolecule can be selected from c-terminal telopeptide antibody, n-terminal telopeptide antibody, alkaline phosphatase antibody, Troponin I antibody and myoglobin antibody. Thus, the avidin is immobilized on the surface of the Au nanoparticles and the biotinylated antibody or aptamer attaches to the avidin.

The process of biotinylation generally includes covalently attaching biotin to a protein, nuclei acid or other molecule. Biotin is known to bind to avidin with high affinity. The antibody or aptamer can be biotinylated chemically or enzymatically using conventional processes and apparatus.

The presence of the selected biomolecule, e.g., biotinylated antibody or aptamer, provides for the detection of the target clinical marker.

In certain embodiments, the biosensors of the invention further include treating the antibody immobilized carbon nanotubes with bovine serum albumin.

The conditions for carbon nanotube electrodeposition and Au nanoparticle functionalization can vary. In general, the Au-coated carbon nanotube electrodes in accordance with the invention may be prepared by growing carbon nanotubes on a substrate, electrodepositing Au on the surface of the carbon nanotubes and treating the Au-coated electrodes with avidin followed by biotinylated antibody or aptamer. The biotinylated antibody can include biotinylated proteins. In certain embodiments, the biotinylated antibody or aptamer is selected based on its ability to interact with tissue markers. Thus, Troponin I antibody or aptamer may be selected to interact with Troponin I biomarker and myoglobin antibody or aptamer may be selected to interact with myoglobin biomarker. In certain other embodiments, the biotinylated antibody or aptamer is selected based on its ability to interact with bone markers. Thus, c-terminal telopeptide antibody or aptamer may be selected to interact with c-terminal telopeptide, n-terminal telopeptide antibody or aptamer may be selected to interact with n-terminal telopeptide, and alkaline phosphatase antibody or aptamer may be selected to interact with alkaline phosphatase. These bone and tissue markers include protein fragments that are released into body fluids, e.g., serum and urine, during bone and tissue remodeling, e.g., bone and tissue resorption, respectively.

Tartrate resistant acid phosphatase (TRAcP) is another biomarker that is released as part of bone and/or tissue resorption. Without intending to be bound by any particular theory, it is believed that TRAcP is capable of degrading carbon nanotubes under in-vitro conditions. Thus, TRAcP has the potential to degrade the impedimetric clinical marker biosensor made of carbon nanotubes such that the biosensor is subject to slow, e.g., controlled, degradation over a period of time.

In certain embodiments, carbon nanotube posts are grown on a Si-wafer using a chemical vapor deposition (CVD) process. The carbon nanotubes may be annealed to remove amorphous carbon that may be present. The annealed posts then may be removed, e.g., peeled, from the Si-wafer, mounted in a non-conducting material, such as but not limit to, epoxy, degassed, and allowed to cure. Typically, the cure is conducted at room temperature. The antibody immobilized carbon nanotubes then may be treated with bovine serum albumin to produce the biosensors.

The biosensors developed in accordance with the invention may function as both ex-situ and in-situ biosensors. Further, the response time for detecting the target clinical marker with ex-situ or in-situ biosensor devices in accordance with the invention can be considerably shorter than the response time for standard ELISA assays in accordance with the prior art.

In certain embodiments, wherein the biosensor is employed ex-situ, a handheld device may be developed. There are various mechanisms that are known in the art to produce a handheld device that may be employed with the biosensor of the invention. A non-limiting example includes a handheld device similar to conventional glucose sensors which are known in the art. The conventional sensors typically include a test strip and a corresponding standard chart or key used to interpret the results displayed on the test strip. The test strip when contacted with a patient specimen can visibly change color based on the presence or amount of glucose contained within the specimen. The particular color change is then compared or matched with a corresponding color on the chart or key which correlates a level of glucose for the color displayed.

For example, in accordance with certain embodiments of the invention, a test strip and corresponding chart may be color-coded wherein particular colors displayed on the test strip correspond to a level or range of levels of a target clinical marker. A body specimen sample, such as urine or blood, is obtained or removed from a patient. At least a portion of the sample is deposited on the test strip. For example, one or more drops of the sample may be applied to the test strip or the test strip may be immersed into the sample. Within a time period, a change in color of at least a portion of the test strip can be visually observed based on the target clinical marker interacting with the test strip, e.g., biosensor. The particular color and/or the intensity of the color change can be compared and matched with the chart or key to determine the level of the target clinical marker in the sample. Based on the visible change of the biosensor, the presence or absence or particular concentration of the target clinical marker is determined efficiently and accurately. The response time may be minutes or even seconds.

In certain embodiments, wherein the biosensor is employed in-situ, an implanted device may be developed. There are various mechanisms that are known in the art to produce an implantable device that may be employed with the biosensor of the invention. A non-limiting example includes a scaffold which is typically used in orthopedic, craniofacial and cardiovascular surgeries. In certain embodiments, the biosensor composite including substrate and gold-coated carbon nanotubes with avidin and biotinylated antibody or aptamer thereon may be applied to the surface of the scaffold. In other certain embodiments, the gold-coated carbon nanotubes with avidin and biotinylated antibody or aptamer thereon may be directly deposited or embedded on the surface of the scaffold to form a biosensor, e.g., the scaffold serves as the substrate on which the carbon nanotubes are grown or deposited. A transmitting device, such as an RFID tag or chip, may be incorporated with the biosensor. The scaffold, biosensor and transmitting device are implanted into the body of a patient. As bone or tissue resorption occurs on the scaffold, the biosensor detects the target bone or tissue marker, and the impedimetric signals are wirelessly transmitted by the transmitting device in or connected to the biosensor to an ex-situ measuring device. The measuring device can determine the presence or absence or level of concentration of the target bone or tissue marker interacting with the biosensor on a measurable display read out. Thus, the read out can confirm the resorption of bone or tissue without requiring x-rays or invasive tests. Further, the read out may be compared to a threshold value or range to determine the extent of bone or tissue resorption in the body.

Further, with respect to the in-situ embodiment, the TRAcP which is a naturally occurring enzyme in the body resulting from bone resorption will be effective to at least contribute to degradation of the carbon nanotube biosensor. Thus, as bone resorption proceeds, TRAcP is produced such that when sufficient bone resorption occurs, the TRAcP can be effective to substantially or completely degrade the carbon nanotube-based biosensor.

In addition to the biosensor being degradable, the scaffold may also be degradable. There is known in the art various materials for constructing implantable devices such that they degrade over a period of time.

In general, an implant device can serve as filler or support material during a natural bone or tissue healing process. Non-limiting examples of implant devices include, but are not limited to, plates, meshes, staples, screws, pins, tacks, rods, suture anchors, tubular mesh, coils, X-ray markers, catheters, endoprostheses, pipes, shields, bolts, clips or plugs, dental implants or devices, graft devices, bone-fracture healing devices, bone replacement devices, joint replacement devices, tissue regeneration devices, cardiovascular stents, nerve guides, surgical implants and wires.

In certain embodiments, the scaffold for use in the invention may be composed and constructed of a biocompatible material that is biodegradable. Suitable biocompatible and biodegradable materials include a wide variety of magnesium-containing materials, e.g., magnesium alloys. Non-limiting examples of suitable materials include those described in PCT Application having International Application No. PCT/US2012/058939 entitled "Biodegradable Metal Alloys" filed on Oct. 5, 2012 and based on U.S. Provisional Patent Application 61/544,127 entitled "Biodegradable Metal Alloys" filed on Oct. 6, 2011; and U.S. patent application Ser. No. 14/045,011 entitled Biodegradable Iron-Containing Compositions, Methods of Preparing and Applications Therefor" filed on Oct. 3, 2013 and based on U.S. Provisional Patent Application 61/710,338 entitled "Biodegradable Iron-Containing Compositions, Methods of Preparing and Applications Therefor" filed on Oct. 5, 2012, which are incorporated in their entirety herein by reference.

In certain embodiments, the scaffold may be constructed of a composition including magnesium and/or iron and one or more of zirconium, manganese, calcium, yttrium and zinc. For example, suitable compositions include a combination, e.g., mixture or blend, of magnesium, iron, manganese and calcium, or a combination, e.g., mixture or blend, of magnesium, iron, zirconium and calcium, or a combination, e.g., mixture or blend, of magnesium, iron zinc and calcium. The amount of each of the components in the combinations/compositions can vary and in general, the amounts are selected such that the resulting combinations/compositions are within acceptable non-toxic limits, sufficiently biocompatible and degradable over a period of time. For example, the components and their amounts may be selected such that the combinations/compositions exhibit corrosion resistance in the presence of water and body fluids which allow for suitable in-vitro use in a physiological environment, e.g., patient body, and exhibit corrosion resistance with minimal or no evolution of hydrogen gas as the evolution of hydrogen, e.g., hydrogen bubbles, may cause complications in a patient body.

In certain embodiments, the composition for use in the invention includes from about 0.5 to about 4.0 weight percent of yttrium, from greater than zero to about 1.0 weight percent of calcium, from about 0.25 to about 1.0 weight percent of zirconium, and the remainder or balance being magnesium based on total weight of the composition. In other embodiments, the composition includes from about 1.0 to about 6.0 weight percent of zinc, from greater than zero to about 1.0 weight percent of zirconium, and the remainder or balance being magnesium based on total weight of the composition.

It is contemplated that other components may be added to the compositions provided that the non-toxicity, biocompatibility and degradability remain within acceptable limits. Acceptable non-toxic limits and time frames for degradation can vary and can depend on the particular physical and physiological characteristics of the patient, in-vitro site of implantation and medical use of the device. Non-limiting examples of suitable other components include aluminum, silver, cerium and/or strontium. In certain embodiments, each of the aluminum, silver, cerium and strontium may be present in an amount from about 1.0 to about 9.0 weight percent, from about 0.25 to about 1.0 weight percent, from about 0.1 to about 1.0 weight percent and from about 1.0 to about 4.0 weight percent, respectively, based on total weight of the composition.

In certain embodiments, the composition includes from about 0.5 to about 4.0 weight percent of yttrium, from greater than zero to about 1.0 weight percent of calcium, from about 0.25 to about 1.0 weight percent of silver, from about 0.25 to about 1.0 weight percent of zirconium, and the remainder or balance being magnesium, based on total weight of the composition.

In other embodiments, the composition includes from about 0.5 to about 4.0 weight percent of yttrium, from greater than zero to about 1.0 weight percent of calcium, from about 0.1 to about 1.0 weight percent of cerium, from about 0.25 to about 1.0 weight percent of zirconium, and the remainder or balance being magnesium, based on total weight of the composition.

In other embodiments, the composition includes from about 0.5 to about 4.0 weight percent of yttrium, from greater than zero to about 1.0 weight percent of calcium, from about 0.25 to about 1.0 weight percent of silver, from about 0.1 to about 1.0 weight percent of cerium, from about 0.25 to about 1.0 weight percent of zirconium, and the remainder or balance being magnesium, based on total weight of the composition.

In yet other embodiments, the composition includes from about 1.0 to about 6.0 weight percent of zinc, from about 0.25 to about 1 weight percent of silver, from greater than zero to about 1.0 weight percent of zirconium, and the remainder or balance being magnesium, based on total weight of the composition.

In still other embodiments, the composition includes from about 1.0 to about 6.0 weight percent of zinc, from about 0.1 to about 1 weight percent of cerium, from greater than zero to about 1.0 weight percent of zirconium, and the remainder or balance being magnesium, based on total weight of the composition.

In still other embodiments, the composition includes from about 1.0 to about 6.0 weight percent zinc, from about 0.25 to about 1 weight percent of silver, from about 0.1 to about 1 weight percent of cerium, from greater than zero to about 1.0 weight percent of zirconium, and the remainder or balance being magnesium, based on total weight of the composition.

In certain embodiments, the compositions for use with the invention include a mixture of one or more elements, such as, Fe, Mn, Mg and Ca. In other embodiments, the compositions include a mixture Fe, Zr, Mg and Ca. In still other embodiments, the compositions include Fe, Zn, Mg and Ca. The elemental iron may be present in an amount such that it constitutes from about 10.0 weight percent to about 95.0 weight percent based on total weight of the composition. The manganese, magnesium and calcium may be each present in an amount such that the manganese constitutes from about 5.0 weight percent to about 75.0 weight percent, the magnesium constitutes from greater than zero weight percent to about 10.0 weight percent, and the calcium constitutes from greater than zero weight percent to about 10.0 weight percent, based on total weight of the composition. The magnesium, zirconium and calcium may be each present in an amount such that the magnesium constitutes from greater than zero weight percent to about 7.0 weight percent, the zirconium constitutes from about 8.0 weight percent to about 52.0 weight percent, and the calcium constitutes from greater than zero weight percent to about 30.0 weight percent, based on total weight of the composition. The magnesium, zinc and calcium may be each present in an amount such that the magnesium constitutes from greater than zero weight percent to about 10.0 weight percent, the zinc constitutes from greater than zero weight percent to about 10.0 weight percent, and the calcium constitutes from greater than zero weight percent to about 30.0 weight percent, based on total weight of the composition.

Suitable scaffolds for use in the invention may be prepared using various methods and processes. The components, e.g., magnesium and one or more of iron, manganese, calcium, zirconium and zinc, may be melted or alloyed at an elevated temperature using conventional methods known in the art. In certain embodiments, the components are alloyed using high energy mechanical alloying (HEMA), uniaxial or isostatic compaction, and sintering. HEMA may be conducted under a protective atmosphere, e.g., in the presence of argon, sulfur hexafluoride and mixtures thereof, to preclude, minimize or reduce decomposition of the components in the composition. Subsequent to HEMA, amorphous films may be synthesized by pulsed laser deposition (PLD).

Further, it is known to use general casting methods and, forming and finishing processes, such as, extrusion, forging, polishing (by mechanical and/or chemical means), surface treating (to form a superficial layer), and combinations thereof, to produce the scaffold for use as an implant device. For example, a molten alloyed composition may be poured into a mold, allowed to cool and thereby solidify.

Thus, both the carbon nanotube-based biosensor and the scaffold can be degraded over a period of time, such as when sufficient bone or tissue resorption has occurred, and therefore obviate the need for invasive surgeries to remove the implanted scaffold and the embedded biosensor.

In certain embodiments, the biosensors of the invention are effective to detect a target clinical marker in concentrations ranging from 0.1 ng/mL to 0.6 ng/mL.

EXAMPLES

Example 1A—CNT Based Biosensor Development and Detection of Bone Marker

Carbon nanotube posts grown on Si-wafers using a CVD process were obtained from the Department of Chemical and Materials Engineering at the University of Cincinnati. The obtained nanotubes were annealed at 400-450° C. for an hour to remove any amorphous carbon present. The annealed posts were peeled individually from the silicon wafer, mounted in non-conducting epoxy, and degassed to remove any bubbles. The individually mounted CNT posts were then allowed to cure under room temperature conditions for approximately 8-12 hours. The epoxy-mounted posts were polished on one end using silicon carbide polishing paper. Electrical contact of the exposed nanotubes with copper wire was made using a silver epoxy paste. Non-conducting epoxy was employed to insulate the region of contact between CNTs and copper wire followed by curing under room temperature conditions. The epoxy was polished sequentially using silicon carbide paper to 5 µm-50 nm to expose the other end of the CNTs, and was cleaned ultrasonically in absolute ethanol and deionized (DI) water for 2-5 minutes. The prepared CNT electrodes were characterized electrochemically by cyclic voltammetry (CV) and electrochemical impedance spectroscopy (EIS) using Gamry Potentiostat.

The CV demonstrated that increasing the deposition time increased the peak currents of the oxidation and reduction reactions. The peak separation voltage for the redox probe was approximately 100 mV for plain CNT post electrode, and reduced with increasing times of gold deposition. The decrease in peak separation voltage and increase in peak currents with the increase in time of gold deposition indicated that increasing gold deposition time considerably improved the electron transfer kinetics of the system. Further, the influence of the square root of scan rate on the peak currents of gold deposited CNT post electrodes was observed. It was shown that the controlled electrode current densities through the area of gold deposited were achieved by varying the electro-deposition times.

The impedance spectrum of plain CNT and Au-CNT post electrodes for varying deposition times and the corresponding equivalent circuit used to model the interface surface was observed. The Nyquist plots demonstrated that the charge transfer resistance decreased with increasing time of gold deposition, indicating very fast electron processes, which were also demonstrated in the cyclic voltammograms.

The electrolyte used for the testing consisted of 5 mM of potassium ferrocyanide/ferricyanide redox coupled in 10 mM phosphate buffer saline (PBS). The electrodes were rinsed in DI water and dried.

Gold was electrodeposited using 0.08 M hydrogen tetrachloaurate solution (Sigma Aldrich) by applying a potential ranging from 0.150-0.200 V Vs. Ag/AgCl reference electrode for 5-60 s. The gold coated electrodes were rinsed in DI water, allowed to dry and then treated with 0.-5-1 mg/mL neutravidin prepared in 10 mM PBS, pH 7.4, for 12-24 hours at 4° C. The avidinated electrodes were then treated with biotinylated C-terminal telopeptide antibody for 12-24 hours at 4° C. It was known that this antibody is specific in its interaction with C-terminal telopeptide. The antibody immobilized electrodes were then treated with 1% bovine serum albumin (BSA) prepared in 10 mM PBS, pH 7.4 for 45-60 minutes. The developed biosensors were then ready for testing. Separate electrodes were prepared for characterization using scanning electron microscopy (SEM, Philips XL30, operating voltage: 5-10 KV).

Based on an SEM image, it was observed that the gold nanoparticles were substantially uniformily electrodeposited over the entire cross-sectional area of the CNT electrode. Further, it was demonstrated that increasing the gold electrodeposition times, i.e., 5, 15, 30 and 60 seconds resulted in a corresponding increase in the size and distribution of the gold nanoparticles.

The developed biosensor was treated with C-terminal telopeptide for an hour under room temperature conditions. Following this, the sensor was rinsed in PBS and tested for change in electrochemical impedance across a frequency range of 300,000-0.1 Hz. For single-frequency testing, the sensor was tested at a single frequency within the range of 10-20 Hz. The sensor interface was regenerated back to its pre-gold pristine state via sonication for refunctionalization and reuse.

The Nyquist impedance spectra upon detection of various concentrations (0.00-0.60 ng/mL) of C-terminal telopeptide by the biosensor was observed. There was a progressive increase in semicircle diameter with increasing concentrations of C-terminal telopeptide that corresponded to antigen-antibody interaction at the electrode interface. Further, the calibration curve based upon the percent change in charge transfer resistance with increase in concentration was observed, and indicated that the developed impedimetric biosensor responded linearly to the antigen concentrations with a correlation coefficient of 0.98. The absolute impedance spectra at a single frequency (18.75 Hz) upon detection of various concentrations of C-terminal telopeptide by the biosensor was observed and demonstrated a progressive increase in magnitude with increasing concentrations. The calibration curve based upon the percent change in absolute impedance with increase in concentration was observed and the impedimetric sensor responded linearly to the antigen concentrations with a correlation coefficient of 0.97. Therefore, the impedimetric biosensor was proven to be capable of detecting C-terminal telopeptide concentrations at a clinically relevant range.

Example 1B—Aptamer-Based CNT-Biosensor for Bone Marker Detection

Another biosensor was developed using an aptamer specific for C-terminal telopeptide. The gold-coated electrodes were treated with 5-50 mM of 11-Mercaptoundecanoic acid (MUA) for 2-18 hours, and were then treated with a 10-100 mM concentration of sulfo-N-hydroxyl-succinimide (NHS) and a 40-400 mM concentration 1-ethyl-3-(3-dimethylaminopropyl) carbodiimide) (EDC) mixed at equal volumes for 15-30 minutes. The sensors were treated with 0.5-1.0 mg/mL Avidin for 1-4 hours, 0.148 µg/mL 148 µg/mL C-terminal telopeptide-specific aptamer for 1-4 hours, and blocked with 1% BSA prepared in 10 mM PBS for 30-45 minutes. The developed biosensor was treated with C-terminal telopeptide for an hour under room temperature conditions. Afterwards, the sensor was rinsed in PBS and tested for change in electrochemical impedance across a frequency range of 300,000-0.1 Hz.

The Nyquist impedance spectra upon detection of various concentrations (0.00-0.60 ng/mL) of C-terminal telopeptide by the use of an aptamer-based (rather than antibody-based) sensor was observed. There was a progressive increase in semicircle diameter with increasing concentrations of C-terminal telopeptide that corresponded to antigen-aptamer interaction at the electrode interface. The calibration curve based upon the percent change in charge transfer resistance with increase in concentration was observed, and indicated that the developed impedimetric biosensor responded linearly to the antigen concentrations with a correlation coefficient of 0.98. It was contemplated that the aptamer may allow for potential regeneration of the aptamer after detection without damaging the remainder of the interface, thus creating a regenerative sensor that can continuously detect antigen concentrations without delay.

Example 2—CNT Degradation Using Bone Marker—Tartrate Resistant Acid Phosphatase (TRAcP)

Example 2A—CNT Treatment with TRAcP

Single-walled carbon nanotubes (P2-SWNTs, Carbon Solutions, Inc. Riverside, Calif.) were carboxylated using piranha solution ($H_2SO_4/H_2O_2$ in the ratio of 3:1) for 24 hours. A vial containing 20-40 µg/100 µL of carboxylated SWNTs (C-SWNTs) was prepared in DI water. To this, 10-20 µl of 0.5-1.0 mg/mL TRAcP in 25 mM Tris and 0.15 mM NaCl, pH 7.5 was added. Further, hydrogen peroxide was added such that the final concentration was 0.2 M. The solution was then regenerated with the addition of 2.5-5.0 µL of 8 mM $H_2O_2$ every hour for up to 4-5 hours. At the end of 5 hours, 10-15 µL of TRAcP and 5-10 µL of $H_2O_2$ was added. After 24 hours, 1-2 µL of 0.1 mM of ascorbic acid was added. This was followed by the addition of 2.5-5 µL of 8 mM $H_2O_2$ every hour for up to 4-5 hours. At the end of 5 hours, 5-10 µL of $H_2O_2$ and 10-15 µL of TRAcP were added. After 24 hours, the procedure involving the addition of ascorbic acid, $H_2O_2$ and TRAcP was repeated. The C-SWNT solutions treated with and without enzyme were characterized using Raman microscopy (Renishaw in Via Raman Microscope) and Transmission electron microscopy (TEM, JEM 2100F).

A first vial containing carboxylated SWNTs (C-SWNTs) treated with TRAcP and a second vial containing carboxylated SWNTs (C-SWNTs) without TRAcP were prepared and observed over a period of 3 days. The one that was treated with the enzyme appeared by visual inspection to be much lighter in color than the carboxylated SWNT solution that was not treated with the enzyme marker. This may have been indicative of potential degradation of the nanotubes by TRAcP under the conditions detailed in Example 2. Although the solution treated with TRAcP appeared lighter in color, the presence of SWNTs in the solution may have been indicative of incomplete degradation reaction. The Raman spectra of the C-SWNTs treated with and without enzyme was observed. The presence of order and disorder peaks was clearly present for the treated C-SWNTs, but were reduced significantly in intensity for the untreated C-SWNTs. The enzyme-treated C-SWNTs also showed that while there was a remnant order band typically present in SWNTs, the disorder band had nearly disappeared, which could have meant that the degradation process essentially began at the defects and carboxylated groups present in SWNTs. The remnant peak corresponding to the order band indicated possible incomplete carboxylation of SWNTs, thereby, insulating it from any reaction or possible orientation towards the enzyme active site for further oxidation and eventual degradation. FIGS. 1A and 1B show the TEM images of untreated and enzyme treated C-SWNTs, respectively. The untreated C-SWNTs clearly show fringes that are indicative of the crystal lattice structure of CNTs. The fringes are less pronounced in FIG. 1B indicating CNT degradation. Further, the images in FIG. 1B show the presence of aggregated spherical units that may be the accumulation of byproducts of CNT degradation.

Example 2B—Molecular Modeling and Docking

The 3-D structure of SWNTs (single-walled nanotubes) was generated using Nanotube Modeler software (v. 1.7.3)

to have a diameter of 1.4 nm and chiral indices (m, n) as (8, 8) and (14, 4) for metallic and semiconducting SWNTs respectively. SWNTs were then modified to contain carboxyl and hydroxyl group using the Builder Tool incorporated in PyMOL visualization software (v. 1.5.05). Modified (carboxylated and hydroxylated) and pristine SWNTs were then docked to the TRAcP X-ray crystal structure (PDB ID: 1WAR, chain A) using the iterated Local Search Global Optimization algorithm provided by AutoDock Vina (v. 1.1.2). The required .pdbqt input files for both the enzyme and the SWNTs were generated using the AutoDock tools package provided by AutoDock4.2. A cubic box was built around the protein with 70×70×70 points as the x, y, and z sizes, with a default AutoDock Vina spacing of 1.000 Å between the grid points. Therefore, the center of the protein, essentially the x, y, and z centers of the cube, were calculated to be 58.562, 20.730, and 46.317, respectively. These given calculated grid maps allowed for the entire surface of the enzyme to be searched for possible binding sites without bias. A total of four CPUs were used to perform the docking, and any other parameters were set as default as defined by AutoDock Vina. The binding conformations given by AutoDock Vina were further analyzed in PyMOL to find the most preferred binding site, the binding energy for the site, and the distances between the SWNT and the catalytic active site of TRAcP.

Figures 2A, 2B, 2C, 2D:
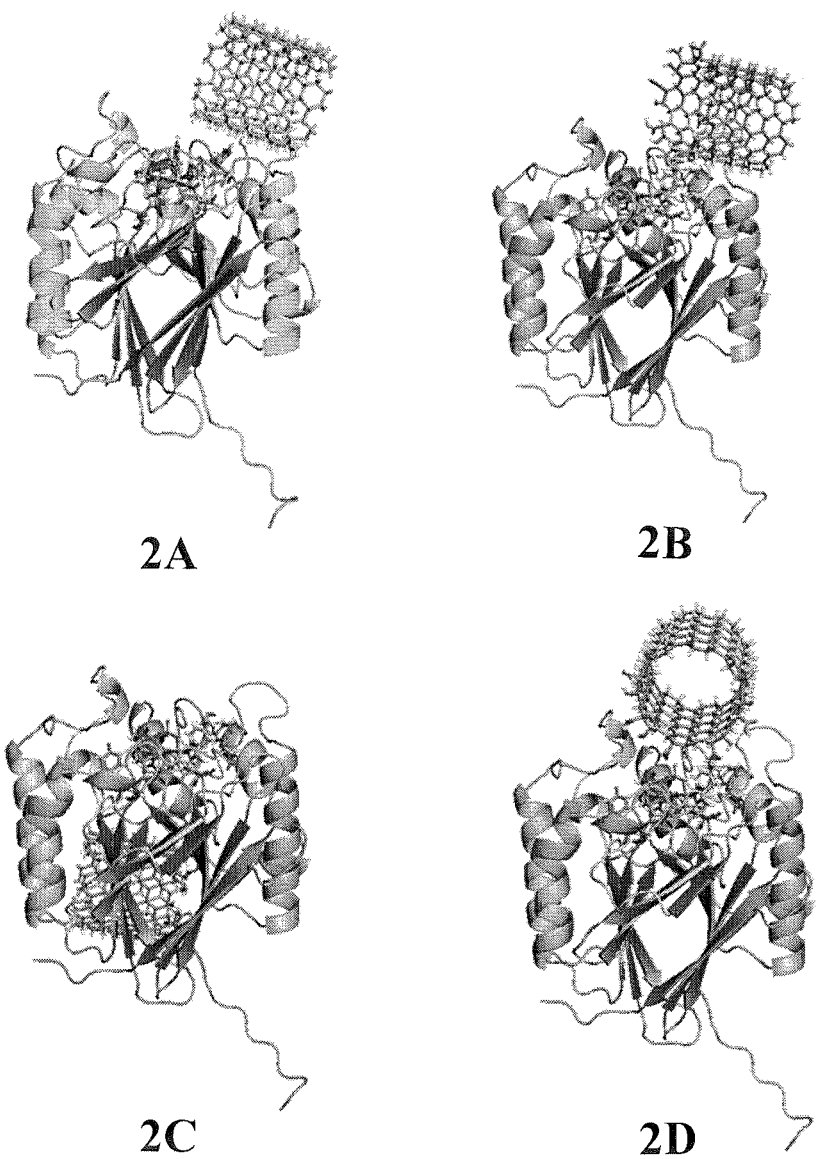
FIGS. 2A, 2B, 2C and 2D show docking conformations of pristine single-walled carbon nanotubes (SWNT), carboxy- lated SWNT with active site orientation, carboxylated SWNT with side orientation and carboxylated SWNT with overhead orientation, in accordance with certain embodiments of the invention.

Molecular modeling was further performed to determine the theoretical orientation of carboxylated and pristine nanotubes with TRAcP. To further clarify the molecular interactions between the SWNTs and TRAcP, various carboxylated and pristine SWNT models of two different chiralities [(8, 8), which were metallic SWNTs, and (14, 4), which were semi-conducting SWNTs] with 1.4 nm diameters and 1.4 nm lengths were generated. These SWNT models were docked to the TRAcP crystal structure (PDB ID: 1WAR, chain A). There were nine complexes that resulted and each was further analyzed to find the best docked conformation, the average binding energy for the best docked conformation, and the distances in angstroms from the catalytic residues of the active site. For pristine SWNTs, there was only one possible docking conformation which is shown in FIG. 2A and Table 1. For modified SWNTs, which had both carboxyl and hydroxyl groups added to the ends, there were three possible docking conformations as shown in FIGS. 2B, 2C and 2D and Table 1. The most dominant docking conformation for both pristine and modified SWNTs was the one oriented towards the dinuclear iron active site. The carboxylated ends of the SWNT were oriented towards the positively charged residue His221 and the phenol-containing residue Tyr53. These residues could potentially be important in stabilizing the binding of the carboxylated/hydroxylated SWNT with the protein and in transfer of electrons from the dinuclear iron active site, respectively. Differences in chirality did not impact orientation or conformation of the SWNTs, implying that both semi-conducting and metallic SWNTS interacted with TRAcP in a similar manner. While the average binding energies for the modified and pristine SWNTs increased (became less negative) with increased carboxylation and hydroxylation, the distances between the carboxyl/hydroxyl groups decreased as the degree of carboxylation of the SWNTs increased as shown in Table 2. Pristine SWNTs had the lowest binding energy (regardless of chirality), but were also located farthest from the residues and dinuclear iron site. Additional modeling was performed to look at the impact of carboxyl and methyl defects introduced into various locations on the SWNTs. These defects were shown to have very little impact on binding energy and distance separation from the active site. Therefore, the data indicated that while helicity of the SWNTs and minor defects within the SWNTs played very little, if any, role in degradation and orientation, the increasing number of surface functionalities was responsible for oxidation and ultimately degradation of SWNTs.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

TABLE 1

| SWNT Modification | Binding Energy (kcal/mol) | Metallic SWNTs | Binding Energy (kcal/mol) | Semiconducting SWNTs |
|---|---|---|---|---|
| Pristine | −10.4 | (9/9) Active Site Orientation | −13.7 | (9/9) Active Site Orientation |
| Pristine + Carboxyl Defect | −10.5 | (7/9) Active Site Orientation (2/9) Side Orientation | −12.9 | (9/9) Active Site Orientation |
| Pristine + Methyl Defect | −10.4 | (9/9) Active Site Orientation | −13.7 | (9/9) Active Site Orientation |
| Single Carboxyl Group | −10.2 | (8/9) Active Site Orientation (1/9) Side Orientation | −11.2 | (8/9) Active Site Orientation (1/9) Side Orientation |
| Four Carboxyl Groups | −9.2 | (9/9) Active Site Orientation | −9.8 | (5/9) Active Site Orientation (4/9) Side Orientation |
| Single-End Carboxylation | −8.1 | (9/9) Active Site Orientation | −7.9 | (7/9) Active Site Orientation (2/9) Side Orientation |
| Single-End Carboxylation + Carboxyl Defect (Center) | −8.1 | (6/9) Active Site Orientation (2/9) Overhead Orientation (1/9) Side Orientation | −7.5 | (4/9) Active Site Orientation (2/9) Overhead Orientation (3/9) Side Orientation |
| Single-End Carboxylation + Methyl Defect (Center) | −8.2 | (9/9) Active Site Orientation | −8.0 | (7/9) Active Site Orientation (2/9) Side Orientation |

TABLE 1-continued

| SWNT Modification | Binding Energy (kcal/mol) | Metallic SWNTs | Binding Energy (kcal/mol) | Semiconducting SWNTs |
|---|---|---|---|---|
| Single-End Carboxylation + Carboxyl Defect (Carboxylated Side) | −8.4 | (9/9) Active Site Orientation | −7.6 | (8/9) Active Site Orientation (1/9) Overhead Orientation |
| Single-End Carboxylation + Carboxyl Defect (Pristine Side) | −8.2 | (8/9) Active Site Orientation (1/9) Overhead Orientation | −7.4 | (5/9) Active Site Orientation (3/9) Overhead Orientation (1/9) Side Orientation |
| Dual End Carboxylation (Fully Carboxylated One End, Two Carboxyl Groups Other End) | −8.3 | (6/9) Active Site Orientation (3/9) Side Orientation | −7.0 | (8/9) Active Site Orientation (1/9) Side Orientation |
| Dual End Carboxylation (Fully Carboxylated Both Ends) | −7.2 | (9/9) Active Site Orientation | −5.5 | (7/9) Active Site Orientation (2/9) Side Orientation |
| Dual End Carboxylation + Carboxyl Defect (Center) | −7.0 | (8/9) Active Site Orientation (1/9) Side Orientation | −5.5 | (7/9) Active Site Orientation (2/9) Side Orientation |
| Dual End Carboxylation + Carboxyl Defect (Carboxylated End) | −7.1 | (8/9) Active Site Orientation (1/9) Side Orientation | −5.4 | (9/9) Active Site Orientation |

TABLE 2

| | SWNT Modification | Distances (Å) | | | | | |
|---|---|---|---|---|---|---|---|
| | | $PO_4$—O1 | $PO_4$—O2 | $PO_4$—O3 | $PO_4$—O4 | $N^{\epsilon 2}$ (His221) | $O^\zeta$ (Tyr53) |
| Metallic SWNTs (8, 8) | P | 5.9 | 6.9 | 8.3 | 7.2 | 7.8 | 8.3 |
| | P + CD (Mid) | 6.0 | 6.9 | 8.4 | 7.1 | 7.5 | 8.7 |
| | P + MD (Mid) | 5.9 | 7.1 | 8.4 | 7.1 | 7.5 | 8.6 |
| | C1 | 5.9 | 6.9 | 8.2 | 7.0 | 7.4 | 8.1 |
| | C4 | 5.3 | 6.5 | 7.7 | 7.0 | 6.8 | 8.1 |
| | C8 | 5.5 | 5.9 | 7.9 | 6.9 | 6.5 | 8.2 |
| | C8 + CD (Mid) | 5.4 | 6.3 | 7.8 | 6.9 | 6.7 | 8.1 |
| | C8 + MD (Mid) | 5.5 | 5.5 | 7.8 | 6.9 | 6.5 | 8.3 |
| | C8 + CD (Mid) | 5.3 | 6.2 | 7.6 | 6.8 | 7.9 | 8.9 |
| | C8 + CD (Pri) | 5.3 | 5.4 | 7.7 | 7.0 | 7.0 | 8.3 |
| | C8C2 | 4.7 | 5.6 | 6.7 | 6.6 | 6.6 | 8.2 |
| | C8C8 | 4.4 | 5.3 | 6.5 | 6.1 | 6.5 | 8.2 |
| | C8C8 + CD (Mid) | 3.8 | 4.7 | 6.0 | 6.6 | 6.4 | 8.4 |
| | C8C8 + CD (Car) | 4.4 | 5.1 | 6.5 | 6.4 | 5.7 | 7.3 |
| Semiconducting SWNTs (14, 4) | P | 6.6 | 7.3 | 8.9 | 7.4 | 7.5 | 8.2 |
| | P + CD (Mid) | 6.4 | 7.2 | 8.7 | 7.3 | 7.7 | 8.4 |
| | P + MD (Mid) | 6.6 | 7.3 | 8.8 | 7.5 | 7.6 | 8.4 |
| | C1 | 6.6 | 7.3 | 8.8 | 7.2 | 7.5 | 8.3 |
| | C4 | 5.9 | 7.2 | 8.2 | 6.5 | 7.0 | 7.7 |
| | C8 | 4.9 | 5.3 | 7.1 | 5.8 | 6.2 | 7.5 |
| | C8 + CD (Mid) | 4.5 | 5.6 | 6.8 | 5.4 | 6.5 | 7.2 |
| | C8 + MD (Mid) | 4.9 | 5.6 | 7.1 | 5.8 | 6.6 | 7.6 |
| | C8 + CD (Mid) | 4.7 | 5.8 | 7.0 | 5.7 | 6.7 | 7.3 |
| | C8 + CD (Pri) | 4.9 | 5.6 | 7.1 | 5.8 | 6.6 | 7.6 |
| | C8C2 | 4.1 | 5.1 | 6.0 | 5.9 | 6.2 | 7.8 |
| | C8C8 | 3.4 | 5.0 | 5.4 | 5.5 | 6.5 | 8.4 |
| | C8C8 + CD (Mid) | 4.0 | 4.8 | 6.2 | 5.3 | 5.3 | 6.9 |
| | C8C8 + CD (Car) | 3.5 | 4.1 | 5.9 | 5.5 | 6.4 | 7.9 |

| | SWNT Modification | Distances (Å) | | | | | | |
|---|---|---|---|---|---|---|---|---|
| | | $Fe_A$ (II) | $Fe_B$ (III) | $N^{\epsilon 2}$ (His184) | $N^{\delta 1}$ (His219) | $O^\delta$ (Asp12) | $O^{\delta 2}$ (Asp50) | $O^{\delta 1}$ (Asn89) |
| Metallic SWNTs (8, 8) | P | 10.2 | 8.8 | 12.4 | 10.9 | 10.4 | 10.1 | 11.1 |
| | P + CD (Mid) | 10.3 | 8.8 | 12.4 | 10.9 | 10.4 | 9.9 | 11.1 |
| | P + MD (Mid) | 10.3 | 8.8 | 12.4 | 11.0 | 10.5 | 10.0 | 11.1 |
| | C1 | 10.2 | 8.8 | 12.2 | 10.9 | 10.4 | 9.9 | 11.1 |
| | C4 | 10.1 | 8.6 | 12.2 | 10.6 | 10.3 | 9.8 | 10.4 |
| | C8 | 9.9 | 8.1 | 11.6 | 10.0 | 9.5 | 9.8 | 10.6 |
| | C8 + CD (Mid) | 9.8 | 8.4 | 12.0 | 10.3 | 9.8 | 9.8 | 10.5 |
| | C8 + MD (Mid) | 9.6 | 8.0 | 11.3 | 9.9 | 10.0 | 9.7 | 10.4 |
| | C8 + CD (Mid) | 9.6 | 8.6 | 11.8 | 9.8 | 9.8 | 9.7 | 10.4 |

TABLE 2-continued

| | | | | | | | | |
|---|---|---|---|---|---|---|---|---|
| | C8 + CD (Pri) | 9.1 | 8.2 | 11.2 | 9.3 | 9.6 | 9.4 | 10.0 |
| | C8C2 | 9.0 | 8.0 | 10.7 | 8.8 | 9.3 | 9.4 | 9.9 |
| | C8C8 | 8.6 | 7.9 | 10.7 | 8.5 | 9.7 | 9.2 | 9.1 |
| | C8C8 + CD (Mid) | 8.1 | 7.7 | 10.3 | 8.5 | 8.9 | 9.1 | 8.8 |
| | C8C8 + CD (Car) | 8.9 | 7.1 | 10.8 | 8.6 | 8.9 | 9.6 | 9.0 |
| Semiconducting SWNTs (14, 4) | P | 10.7 | 8.8 | 12.7 | 11.4 | 10.5 | 10.2 | 11.7 |
| | P + CD (Mid) | 10.5 | 8.8 | 12.6 | 11.3 | 10.6 | 10.3 | 11.6 |
| | P + MD (Mid) | 10.6 | 8.8 | 12.5 | 11.4 | 10.5 | 10.1 | 11.7 |
| | C1 | 10.5 | 8.7 | 12.5 | 11.4 | 10.5 | 10.1 | 11.7 |
| | C4 | 9.9 | 8.1 | 11.9 | 11.0 | 10.0 | 9.3 | 10.9 |
| | C8 | 8.8 | 7.3 | 10.9 | 9.4 | 9.1 | 8.8 | 10.0 |
| | C8 + CD (Mid) | 8.7 | 7.2 | 10.7 | 9.6 | 9.1 | 8.3 | 9.7 |
| | C8 + MD (Mid) | 8.9 | 7.5 | 11.0 | 9.7 | 9.3 | 8.8 | 10.0 |
| | C8 + CD (Mid) | 8.9 | 7.4 | 10.9 | 9.8 | 9.3 | 8.5 | 9.9 |
| | C8 + CD (Pri) | 8.9 | 7.5 | 11.0 | 9.7 | 9.3 | 8.8 | 10.0 |
| | C8C2 | 7.8 | 7.4 | 9.9 | 8.3 | 9.1 | 8.8 | 9.0 |
| | C8C8 | 7.6 | 7.6 | 9.7 | 8.0 | 9.7 | 7.9 | 7.7 |
| | C8C8 + CD (Mid) | 8.3 | 6.6 | 10.3 | 8.9 | 8.3 | 8.2 | 8.9 |
| | C8C8 + CD (Car) | 7.8 | 7.4 | 9.9 | 7.9 | 9.1 | 8.0 | 8.4 |

The invention claimed is:

1. An in-situ, impedimetric biodegradable biosensor to detect a target clinical marker in a body of a patient, comprising:
 a biodegradable scaffold structured to be implanted in the body of the patient, having a surface;
 a plurality of carbon nanotubes, having an outer surface, deposited on the surface of the scaffold;
 a plurality of gold nanoparticles electrodeposited on the outer surface of the plurality of carbon nanotubes;
 a binding material adsorbed on the plurality of gold nanoparticles; and
 a biotinylated biomolecule selected from the group consisting of antibody and aptamer, to bind with the binding material and interact with the target clinical marker selected from the group consisting of a bone marker and a tissue marker.

2. The in-situ, impedimetric biodegradable biosensor of claim 1, wherein the biotinylated biomolecule is aptamer.

3. The in-situ, impedimetric biodegradable biosensor of claim 1, wherein the plurality of carbon nanotubes is deposited directly on the surface of the scaffold.

4. The in-situ, impedimetric biodegradable biosensor of claim 1, wherein the biotinylated biomolecule is antibody.

5. The in-situ, impedimetric biodegradable biosensor of claim 4, wherein the antibody interacts with the target clinical marker selected from the group consisting of c-terminal telopeptide, n-terminal telopeptide, alkaline phosphatase, Troponin I and myoglobin.

6. The in-situ, impedimetric biodegradable biosensor of claim 1, wherein the binding material is selected from the group consisting of avidin, neutravidin and mixtures thereof.

7. The in-situ, impedimetric biodegradable biosensor of claim 1, wherein the plurality of carbon nanotubes is deposited directly on a surface of a substrate comprising silicon, and the substrate is applied to the surface of the scaffold.

8. The in-situ, impedimetric biodegradable biosensor of claim 1, wherein the target clinical marker is Tartrate resistant acid phosphatase.

9. The in-situ, impedimetric biodegradable biosensor of claim 8, wherein degradation results from interaction with the Tartrate resistant acid phosphatase.

* * * * *